United States Patent [19]

Ito

[11] Patent Number: 4,714,554

[45] Date of Patent: Dec. 22, 1987

[54] CROSS-AXIS SYNCHRONOUS FLOW-THROUGH COIL PLANET CENTRIFUGE FREE OF ROTARY SEALS: APPARATUS AND METHOD FOR PERFORMING COUNTERCURRENT CHROMATOGRAPHY

[75] Inventor: Yoichiro Ito, Bethesda, Md.

[73] Assignee: The United States of America as represented by the Department of Health and Human Services, Washington, D.C.

[21] Appl. No.: 915,797

[22] Filed: Oct. 3, 1986

[51] Int. Cl.$^4$ ............................................. B01D 15/08
[52] U.S. Cl. ................................... 210/635; 210/657; 210/198.2
[58] Field of Search ..................... 210/635, 657, 198.2, 210/198.3

[56] References Cited

U.S. PATENT DOCUMENTS

| | | | |
|---|---|---|---|
| 3,775,309 | 11/1973 | Ito | 210/635 |
| 3,856,669 | 12/1974 | Ito | 210/657 |
| 3,994,805 | 11/1976 | Ito | 210/198.2 |
| 4,051,025 | 9/1977 | Ito | 210/657 |
| 4,058,460 | 11/1977 | Ito | 210/198.2 |
| 4,151,089 | 4/1979 | Ito | 210/198.2 |
| 4,162,761 | 7/1979 | Ito | 210/198.2 |
| 4,182,678 | 1/1980 | Ito | 210/198.2 |
| 4,228,009 | 10/1980 | Ito | 210/198.2 |
| 4,228,950 | 10/1980 | Ito | 210/672 |
| 4,321,138 | 3/1982 | Ito | 210/198.2 |
| 4,324,661 | 4/1982 | Ito | 210/657 |
| 4,414,108 | 11/1983 | Ito | 210/198.2 |
| 4,430,216 | 2/1984 | Ito | 210/198.2 |
| 4,487,693 | 12/1984 | Ito | 210/657 |
| 4,532,039 | 7/1985 | Ito | 210/198.2 |
| 4,615,805 | 10/1986 | Ito | 210/657 |

OTHER PUBLICATIONS

Ito, "Application of the Elution Centrifuge to Separation of Polynucleotides with the Use of Polymer Phase Systems Science, vol. 182, pp. 391–393 (1973).
Perry's Chemical Engineer's Handbook, Fourth Edition McGraw Hill, 1969, pp. 24–87 and 24–88.
Ito, New Continuous Extraction Method with a Coil Planet Centrifuge Journal of Chromatography, 207 (1981) 161–169.

Primary Examiner—Ernest G. Therkorn
Attorney, Agent, or Firm—Browdy and Neimark

[57] ABSTRACT

Countercurrent chromatography is performed with an apparatus producing a hitherto unused mode of synchronous planetary motion. The axis of rotation remains tangent to the path of revolution about the axis of rotation. By this planetary motion, symmetrically distributed force vectors are created.

17 Claims, 17 Drawing Figures

| NEW NOMENCLATURE OF SYNCHRONOUS PLANETARY MOTION (OLD TERMS) | ANGLE ψ | PLANETARY MOTION AND REFERENCE COORDINATE FRAME | FORCE DISTRIBUTION DIAGRAM |
| --- | --- | --- | --- |
| TYPE I (SCHEME I) | 180° | | |
| TYPE I-L (SCHEME II) | 135° | | |
| TYPE L (SCHEME III) | 90° | | |
| TYPE J-L | 45° | | |
| TYPE J (SCHEME IV) | 0° | | |

CROSS-AXIS SYNCHRONOUS FLOW-THROUGH COIL PLANET CENTRIFUGE FREE OF ROTARY SEALS: APPARATUS AND METHOD FOR PERFORMING COUNTERCURRENT CHROMATOGRAPHY

FIELD OF THE INVENTION

This invention relates generally to chromatography and more specifically to countercurrent chromatography. cl BACKGROUND OF THE INVENTION Countercurrent chromatography (CCC) utilizes complex hydrodynamic interaction of two immiscible solvent phases in a tubular column space free of solid support. Retention of the stationary phase and solute partitioning take place in an open column space by the aid of a suitable acceleration field particularly provided by coil planet centrifugation. In the past, a series of flow-through centrifuge systems has been developed for performing CCC. Among those, the most useful systems were found to be the coil planet centrifuges which produce synchronous planetary motion of the column holder.

Figure 1:
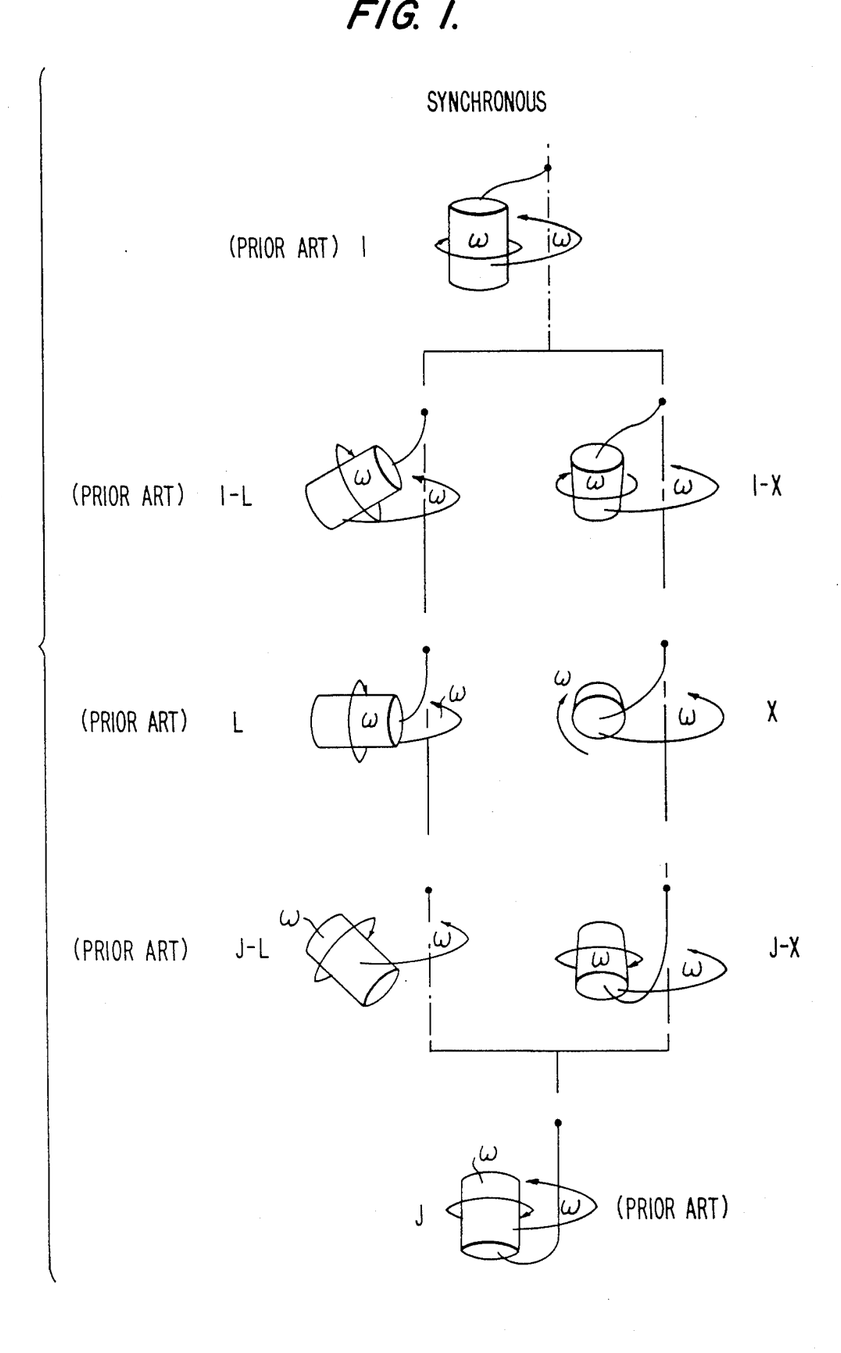
FIG. 1 shows various planetary motion schemes.

FIG. 1 shows the orientation and motion of a cylindrical coil holder under various types of the synchronous planetary motion. In Type I, the holder revolves around the central axis of the centrifuge system while it synchronously counterrotates about its own axis at the same angular velocity. This synchronous counterrotation of the holder steadily unwinds the twist of the flow tubes made by revolution, thus totally eliminating the need for the conventional rotary seal device. This twist free flow-through mechanism works equally well in other synchronous planetary motions with tilted (Types I-L and I-X), horizontal (Types L and X), dipping (Types J-L and J-X), and inverted (Type J) orientations of the holder. Among those planetary centrifuge systems, Type I (U.S. Pat. No. 3,775,309), Type I-L (U.S. Pat. No. 3,994,805), Type L (U.S. Pat. No. 3,856,669), Type J-L (U.S. Patent pending), Type J (U.S. Pat. No. 4,058,460), have been constructed for examination of their performance in CCC. The overall results clearly indicated that Types J and J-L produced the unilateral hydrodynamic distribution of the two solvent phases in the coiled column and are ideal for performing high-speed CCC which is characterized by high peak resolution and excellent retention of the stationary phase against a high flow rate of the mobile phase. This unique performance of these two centrifuge systems are apparently derived from the particular pattern of the acceleration field generated by the planetary motion of the holder.

Figure 2:
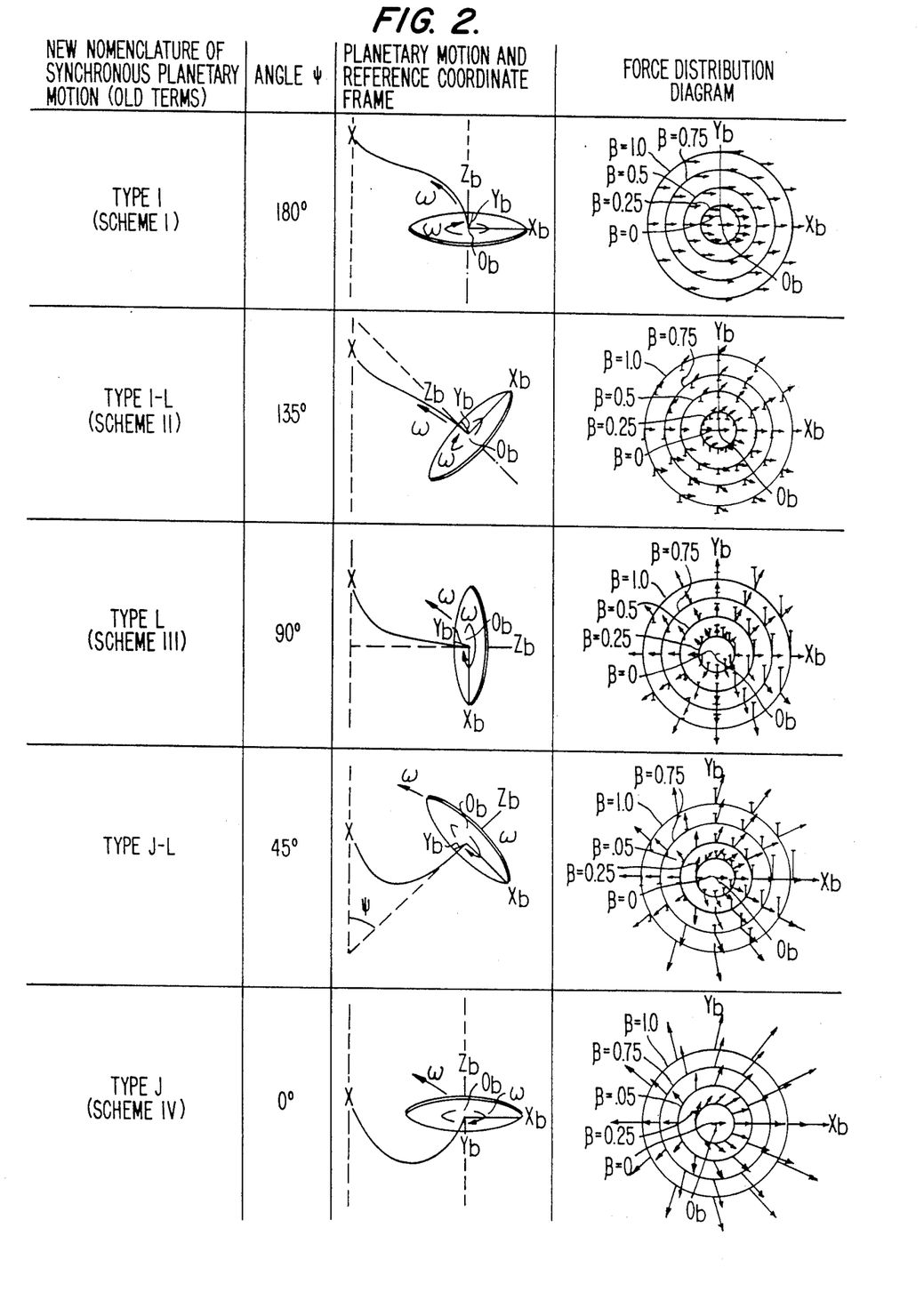
FIG. 2 shows the angle, planetary motion, reference coordinate frame and force distribution for the planetary motion schemes shown in FIG. 1.

FIG. 2 illustrates the distribution of the centrifugal force vectors in those five types of the synchronous planetary motion. In each force distribution diagram, three dimensional orientation of the force vector is expressed in two force components, one acting in the $X_b$-$Y_b$ plane (shown by arrows) and the other acting along the $Z_b$-axis (shown by vertical columns) according to the reference $X_b$-$Y_b$-$Z_b$ coordinate system indicated for each planetary motion. The force distribution diagrams for Type J-L and Type J show asymmetrical distribution of strong radial force components, which is considered to be the cause for the unilateral hydrodynamic distribution of the two solvent phases in the rotating column. The second force component acting along the $Z_b$-axis (columns) in Type J-L is also considered beneficial for introducing efficient mixing of the two solvent phases or improving the retention of the stationary phase depending on the configuration of the coiled column on the rotating holder.

OBJECTS OF THE INVENTION

It is an object of the present invention to provide a method and apparatus for countercurrent chromatography which efficiently mixes solvent phases.

It is another object of the present invention to provide a method and apparatus for countercurrent chromatography which avoids the use of rotary seals.

It is a further object of the present invention to provide a method and apparatus for countercurrent chromatography which produce a highly asymmetrical force distribution pattern along the $X_b$ axis and a symmetrical force distribution pattern along the $Z_b$ axis.

SUMMARY OF THE INVENTION

The present invention is based on a new type of the synchronous planetary motion, Type X, illustrated in FIG. 1. As indicated by its name, the two axes of the centrifuge system, i.e., the axis of the centrifuge (axis of revolution) and the axis of the holder (axis of rotation) cross each other at a 90° angle if viewed sideways.

BRIEF DESCRIPTION OF THE PREFERRED EMBODIMENTS

Figure 3A:
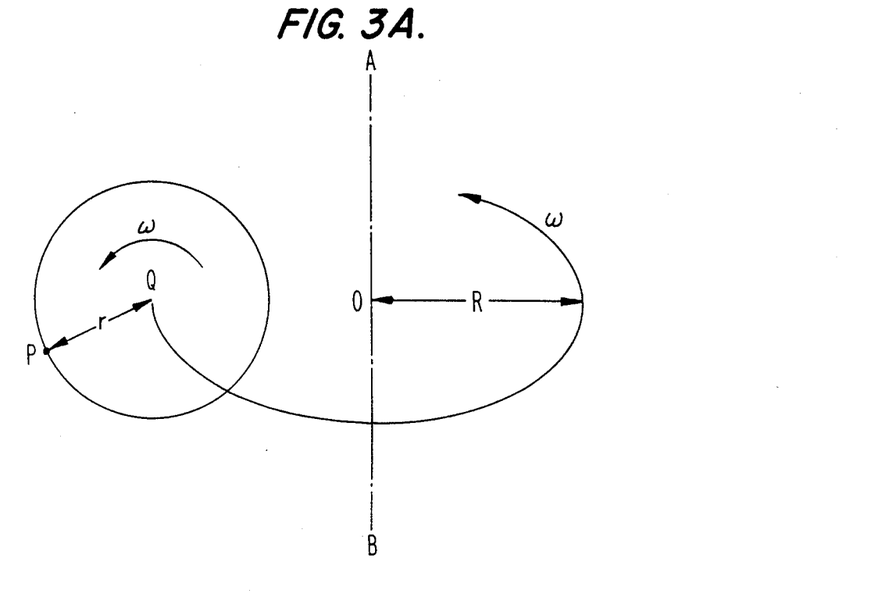
FIG. 3A schematically illustrates synchronous planetary motion of a point P on a centrifuge.

Mathematical analysis of acceleration produced by this new synchronous planetary motion is performed as follows:

Consider a discoid body with radius r and undergoing a planetary motion in such a way that it revolves around the central axis of the centrifuge $(\overline{AB})$ and simultaneously rotates about its own axis (Q) at the same angular velocity ($\omega$) as illustrated in FIG. 3A. in so doing, the discoid body always maintains its face parallel to and at the same distance ($\overline{OQ}=R$) away from the central axis. Then, it is useful to study the motion of an arbitrary point (P) located at the periphery of the discoid body ($\overline{QP}=r$).

Figure 3B:
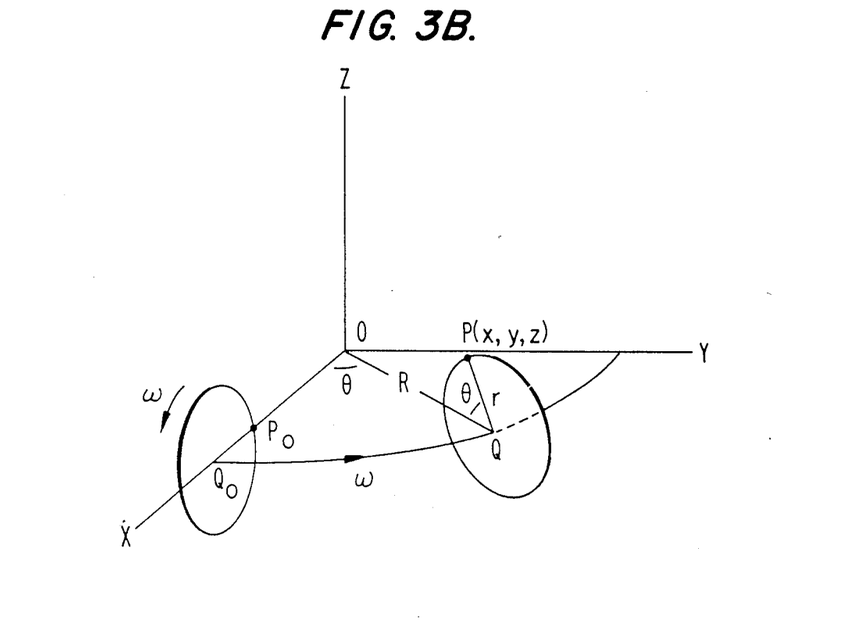
FIG. 3B schematically illustrates the synchronous planetary motion of the point P on a centrifuge according to the present invention, in the x-y-z coordinate system.

FIG. 3B shows an x-y-z coordinate system where z-axis coincides with the central axis and the center of the discoid body (Q) circles around point O in the x-y plane. The arbitrary point on the discoid body and the center of the discoid body are initially located on the x-axis at $P_o$ and $Q_o$, respectively. The discoid body undergoes a synchronous planetary motion as described above: The body revolves around the z-axis and rotates about its own axis at the same angular velocity, $\omega$. After a lapse of time t, the arbitrary point moves to point P and the center of the discoid body to point Q. Then the location of point P (x, y, z) is expressed in the following equations:

$$x = R\cos\theta - r\cos^2\theta \quad (1)$$

$$y = R\sin\theta - r\sin\theta\cos\theta \quad (2)$$

$$z = r\sin\theta \quad (3)$$

where $R=\overline{OQ}$, $r=\overline{QP}$ and $\theta=\omega t$.

The acceleration acting on the arbitrary point is then given by the second derivatives of these equations and $$d^2x/dt^2 = -R\omega^2\cos\theta + 2r\omega^2\cos 2\theta = -R\omega^2(\cos\theta - 2\beta\cos 2\theta) \quad (4)$$

$$d^2y/dt^2 = -R\omega^2\sin\theta + 2r\omega^2\sin 2\theta = -R\omega^2(\sin\theta - 2\beta\sin 2\theta) \quad (5)$$

$$d^2z/dt^2 = -r\omega^2\sin\theta = -R\omega^2\beta\sin\theta \quad (6)$$

where $\beta = r/R$.

Figure 3C:
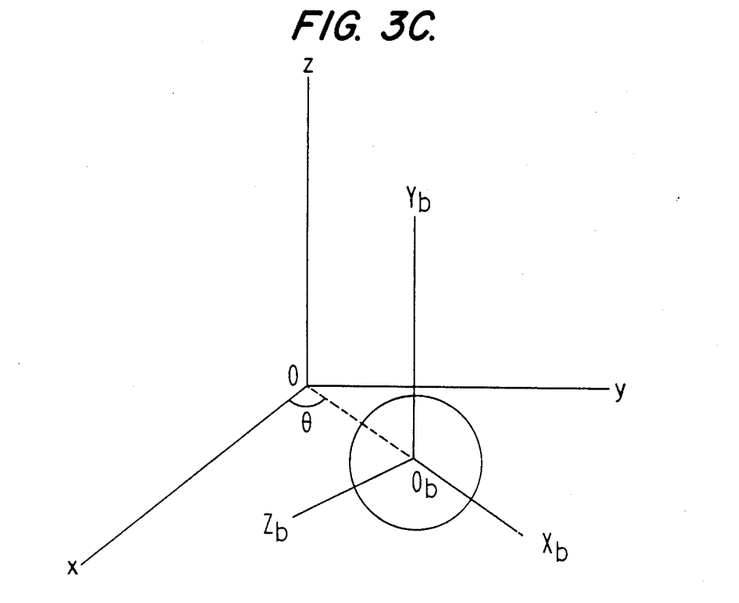
FIG. 3C schematically illustrates the motion illustrated in FIG. 3B, in the $X_b$-$Y_b$-$Z_b$ coordinate system.

In order to visualize the effects of acceleration on the objects rotating with the discoid body, it is more convenient to express the acceleration vectors with respect to the body frame or the $X_b$-$Y_b$-$Z_b$ coordinate system illustrated in FIG. 3C. Transformation of the vectors from the original x-y-z coordinate system to the $X_b$-$Y_b$-$Z_b$ coordinate system may be performed according to the following equations.

$$a_{Xb} = (d^2x/dt^2)\cos\theta + (d^2y/dt^2)\sin\theta = -R\omega^2(1-2\beta\cos\theta) \quad (7)$$

$$a_{Yb} = d^2z/dt^2 = -R\omega^2\beta\sin\theta \quad (8)$$

$$a_{Zb} = (d^2x/dt^2)\sin\theta - (d^2y/dt^2)\cos\theta = -R\omega^2 2\beta\sin\theta \quad (9)$$

where $a_{Xb}$, $a_{Yb}$, and $a_{Zb}$ indicate the acceleration vectors acting along the corresponding coordinate axes.

Figure 3D:
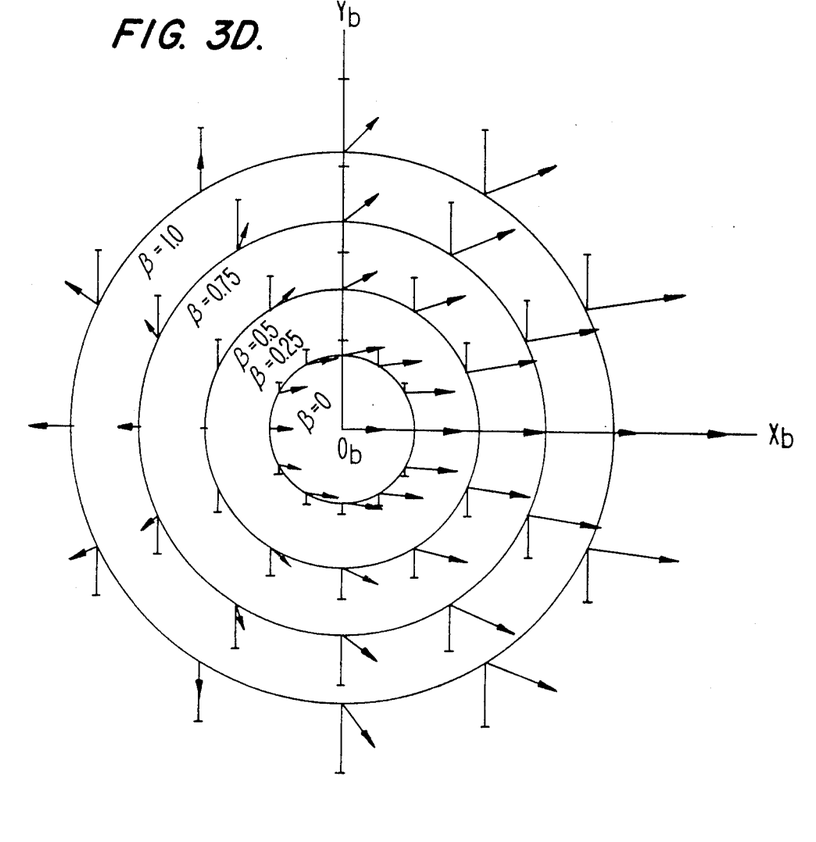
FIG. 3D schematically illustrates force vectors arising in the method and apparatus of the present invention.

From Equations b 7–9, the centrifugal force vectors (same magnitude with the acceleration acting in the opposite direction) at various points on the discoid body are computed and diagrammatically illustrated in FIG. 3D. In order to illustrate the three-dimensional pattern of the centrifugal force vectors on a two-dimensional diagram, two force vectors, $-a_{Xb}$ and $-a_{Yb}$ are combined into a single vector forming various angles from the x-axis, whereas the third force vector, $-a_{Zb}$, which acts perpendicularly to the $X_b$-$Y_b$ plane, is drawn in the vertical direction along the $Y_b$-axis. The ascending column indicates the force acting upward (Z>0) and the descending column, the force acting downward (Z<0). Several concentric circles around point $0_b$ (the center of the discoid body) indicate the location on the discoid body corresponding to various $\beta$ values labelled in the diagram.

The force distribution diagram (FIG. 3D) for the present system resembles those obtained from the Types J and J-L synchronous planetary motions (FIG. 2). This finding strongly suggests that the present system is capable of performing highspeed CCC with a multilayer coil. In comparison with the Type J-L planetary motion, the present system, produces symmetrical distribution of the second components (columns) promising that the system would provide more thorough mixing of the two solvent phases in the column. This efficient mixing is extremely important for the application of different types of the separation column such as eccentric coil assembly and toroidal coil. The force distribution pattern of the present system also suggests that large preparative-scale separations can be efficiently performed by applying slow rotation of a large diameter coil. In this manner gravity acts to retain the stationary phase in the column while the second force component acting along the $Z_b$-axis introduces efficient mixing of the two solvent phases across the diameter of the tube to reduce mass transfer resistance with minimum sample band broadening. The system may also be applied to dual CCC where two solvent phases literally undergo countercurrent flow through the coiled column while the sample is continuously fed through the sample feed line connected at the middle portion of the column. Although this operation requires five flow tubes, the present system permits the use of multiple flow tubes without risk of leakage or cross contamination caused by the use of conventional rotary seals.

The above force distribution analysis was performed on the plane through the center of the discoid body. The force distribution diagrams for other planes away from the above central plane show some changes only in the second components (columns) which develop uneven distribution between the above and below the $X_b$-$Y_b$ plane (the $Z_b$ axis). Although this asymmetry of the force distribution may not significantly affect the separation, the effect can be minimized by applying a column holder with a narrow width.

DETAILED DESCRIPTION OF THE PREFERRED EMBODIMENTS

Figure 4A:
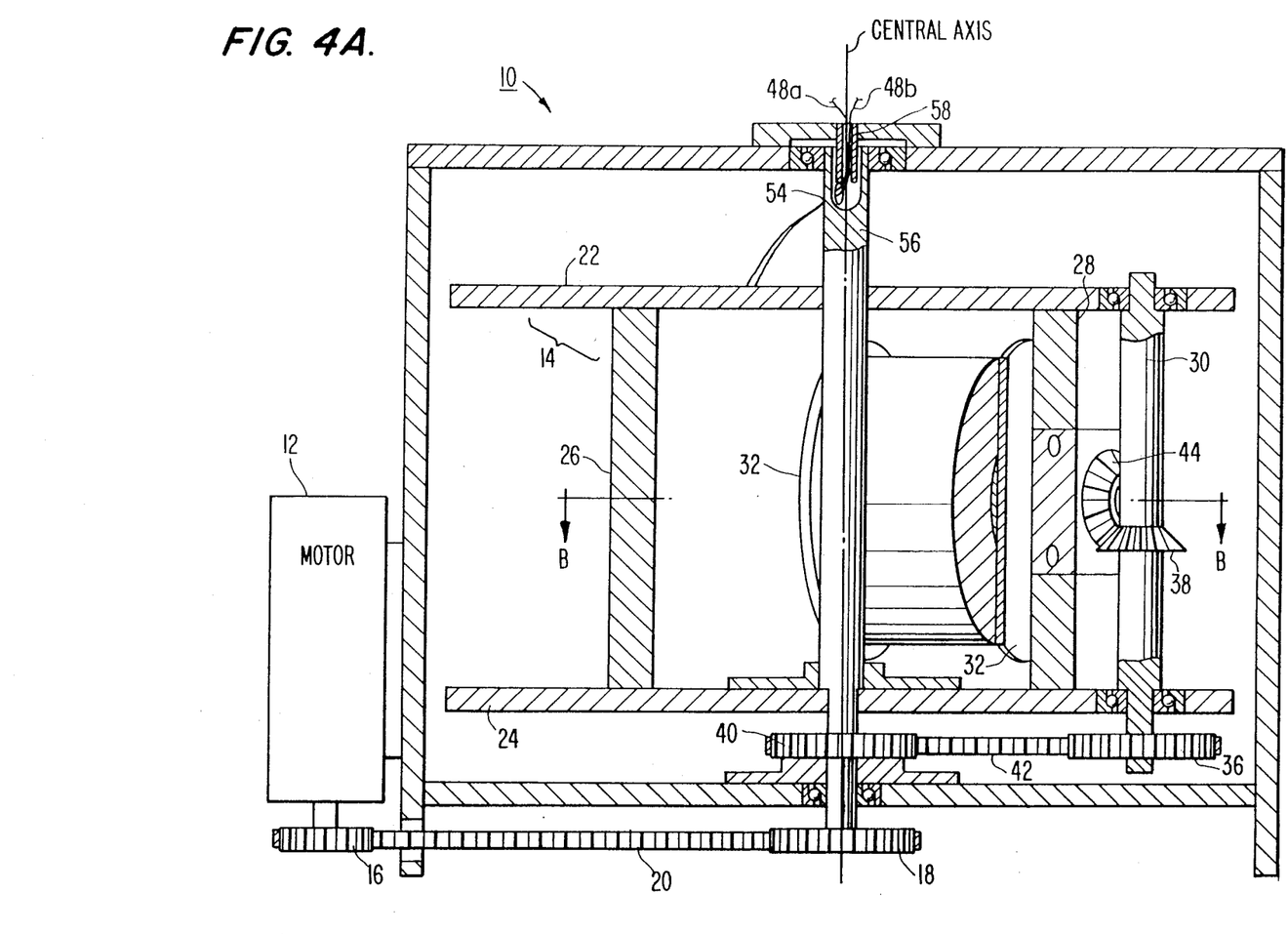
FIG. 4A is a side elevation of a preferred apparatus according to the present invention.
Figure 4B:
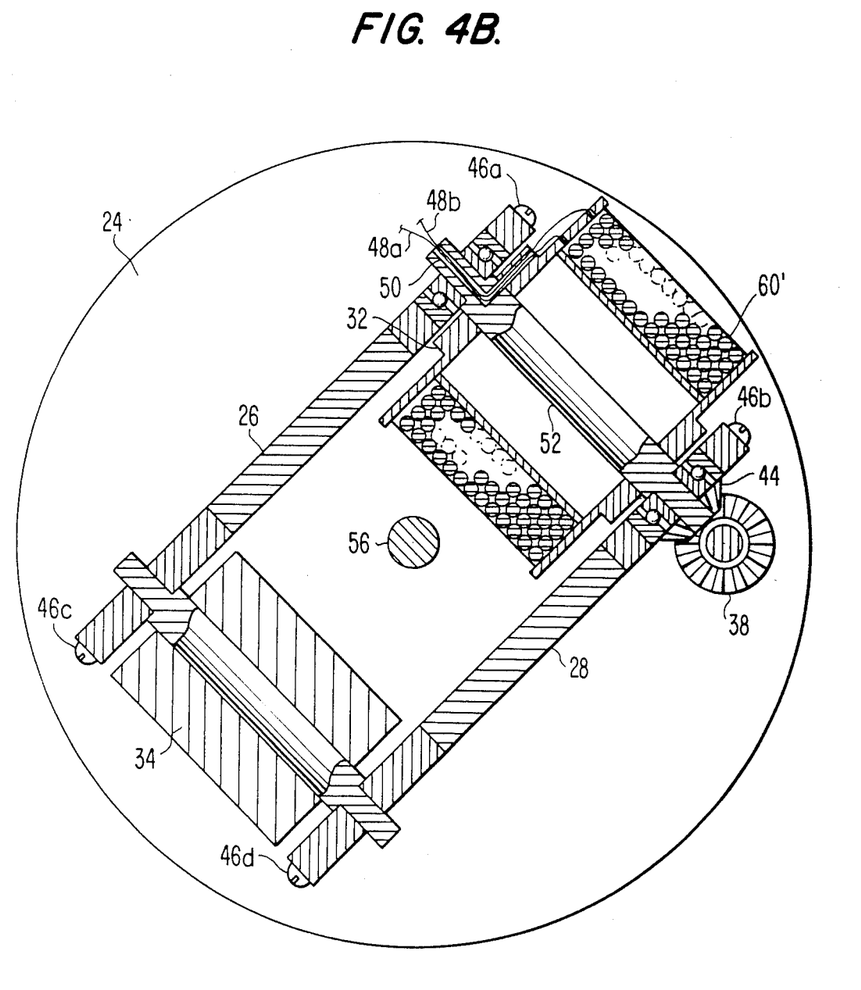
FIG. 4B is a cross-section of the apparatus of FIG. 4A, taken along line B—B.

One example of the design of the cross-axis synchronous coil planet centrifuge is shown in FIGS. 4A and 4B. FIG. 4A illustrates a cross-sectional view across the central axis of the centrifuge 10. The motor 12 (left) drives the rotary frame 14 around the vertical axis of the centrifuge by a pair of toothed pulleys 16, 18 coupled with a toothed belt 20. The rotary frame 14 consists of upper and lower aluminum plates 22 and 24, respectively, rigidly bridged together with a pair of side plates 26, 28, and holds a countershaft 30 (right) and a column holder 32 on one side and a counterweight holder 34 on the opposite side for balancing the centrifuge system 10 (see FIG. 4B). The countershaft 30 is equipped with a toothed pulley 36 at the bottom and a miter gear 38 in its middle portion. The stationary pulley 40 mounted on the central axis of the centrifuge 109 is coupled with a toothed belt 42 to the identical toothed pulley 36 mounted at the bottom of the countershaft 30. This pulley coupling causes synchronous counterrotation of the countershaft 30 on the revolving rotary frame 14. This motion of the countershaft 30 is further conveyed to the column holder 32 by coupling a pair of identical miter gears 38, 44, one mounted on the countershaft and the other on the column holder shaft. Consequently, the column holder 32 rotates about its own axis at an angular velocity equal to that of revolution as previously described in FIG. 3A.

FIG. 4B shows a cross-sectional view through the central axis of the column holder. The column holder and the counterweight holder are symmetrically positioned to balance the centrifuge system. Both holders 32, 34 can be removed from the rotary frame by loosening a pair of screws 46a, 46b. A pair of flow tubes 48a, 48b from the holder 32 is first passed through the hole 50 on the holder shaft 52 and then through the side hole 54 made on the central shaft 56 where it is supported by a stationary tube support 58 projecting down from the center of the centrifuge 10 top. As described earlier, these flow tubes are free from twisting.

Figure 5A:
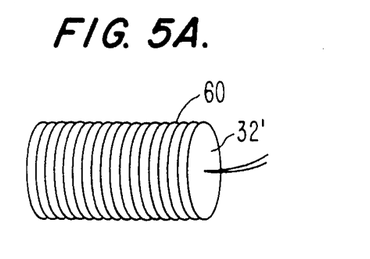
FIGS. 5A–5D illustrate various coil windings useful in the present invention.
Figure 5B:
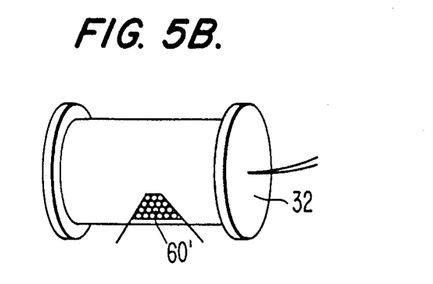
Figure 5C:
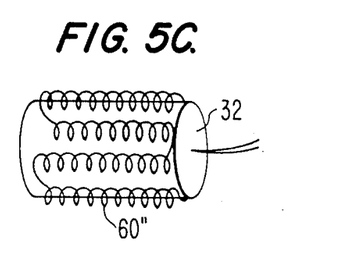
Figure 5D:
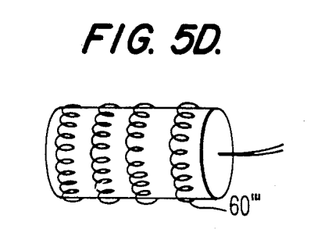
Figure 5E:
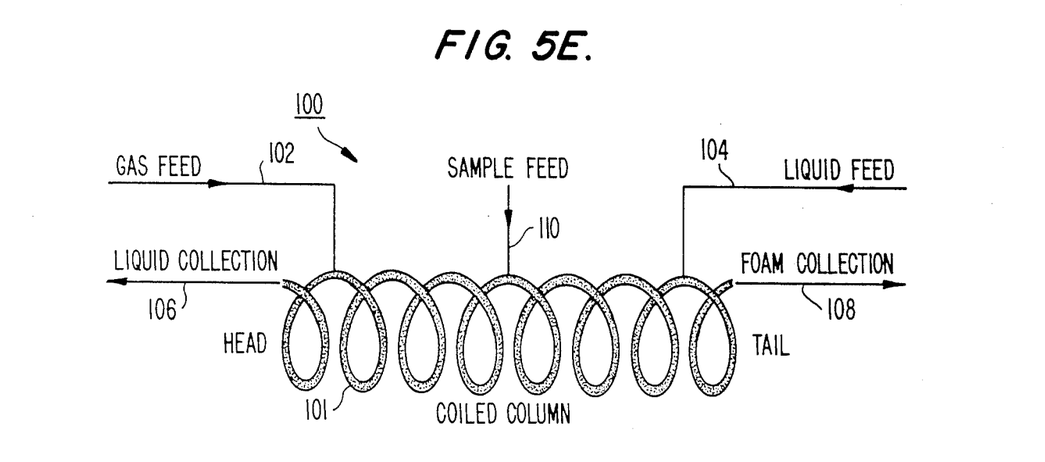
FIG. 5E schematically illustrates a column design for foam countercurrent column chromatography.

FIGS. 5A–5E schematically illustrates various types of coiled columns used with the present apparatus. FIG. 5A is a single layer coil 60 coaxially mounted around the holder 32. This type of the column is useful for continuous extraction of the biological compounds present in a large volume of the sample solution. FIG. 5B shows a multilayer coil 60' coaxially mounted around the spool-shaped holder 32 (also shown in FIG. 4B). This column configuration is capable of yielding highly efficient chromatographic separations in a short period of time and therefore used for performing high-speed CCC. FIG. 5C shows an eccentric coil assembly 60" which is made by connecting multiple units of coils in series and arranging it around the holder 32. This column enables retention of viscous butanol solvent systems and therefore is particularly useful for separations of polar compounds such as peptides. FIGS. 5D is called a toroidal coil and prepared by winding a fine coiled column 60'" around the holder 32. This column is most useful for analytical-scale separations. FIG. 5E schematically shows the layout 100 of the coiled column 101 for dual CCC including liquid-liquid dual CCC and foam CCC. As shown in the diagram, the column is equipped with five flow lines (102, 104, 106, 108, 110), i.e., inlet (102, 104) and outlet (106, 108) lines opening at each end and a sample feed line (110) at the middle portion of the column 101.

Figure 6A:
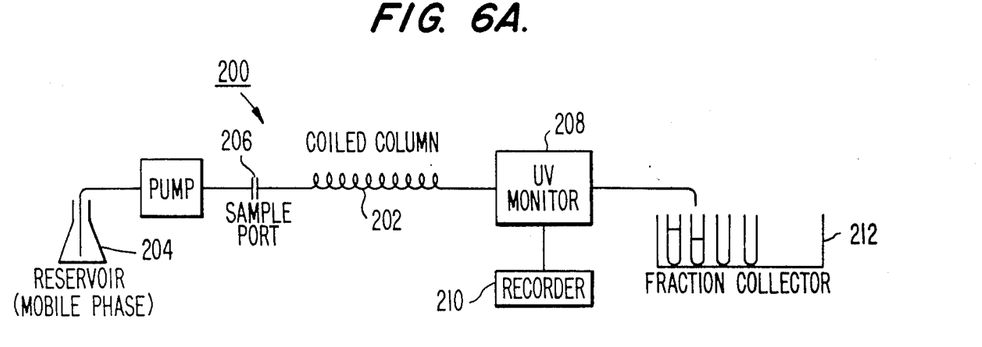
FIGS. 6A–6C schematically illustrate preferred separation schemes for use with the present invention.
Figure 6B:
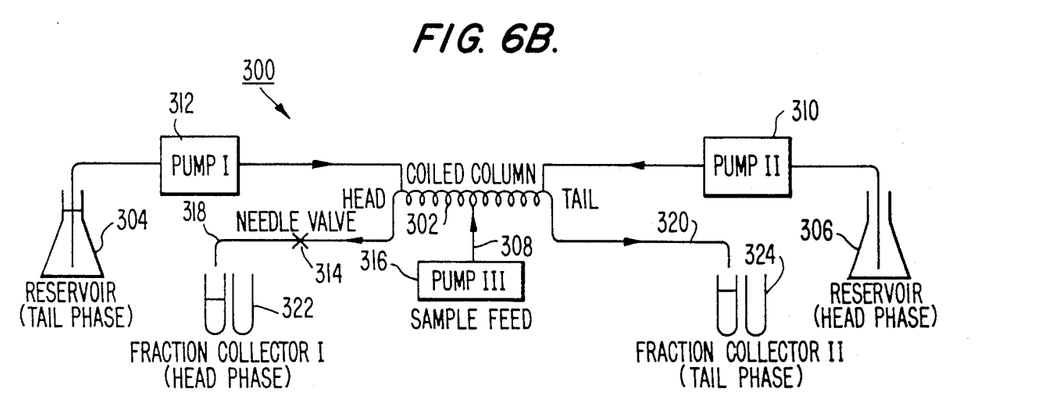
Figure 6C:
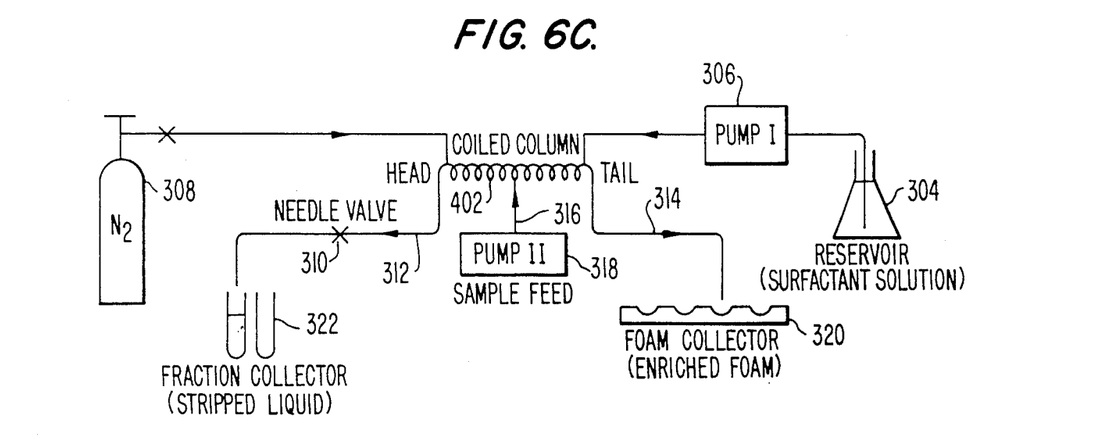

FIGS. 6A–6C diagrammatically illustrate three modes of operation for the cross-axis synchronous flow-through coil planet centrifuge. The standard setup 200 for performing high-speed CCC is shown in FIG. 6A. The column 202 is first entirely filled with the stationary phase and the sample solution 204 is injected through the sample port 206. Then the column 202 is spun at the desired revolutional speed (usually at 800 rpm) while the mobile phase is eluted through the column in the proper mode, i.e., the head phase from the tail toward the head or the tail phase from the head toward the tail. The effluent from the outlet of the column is continuously monitored with a uv monitor 208 (the monitored reading being recorded on recorder 210) and then fractionated with a fraction collector 212.

FIGS. 6B and 6C show dual CCC operation using a coiled column with five flow lines. In liquid-liquid dual countercurrent operation (FIGS. 6B), the column 302 is first entirely filled with either phase 304, 306 or the mixture of both phases, while the sample feed line 308 is closed. Then the head phase 306 and the tail phase 304 are simultaneously fed from the tail (pump II) 310 and the head (pump I) 312 of the column 302, respectively, while the column 302 is rotated at the desired speed. The opening of the needle valve 314 on the head side is adjusted in such a way that the eluting rate through the valve 314 is equal to the feeding rate from the tail end (pump II) 310. After the steady state hydrodynamic equilibrium is reached, the sample solution is introduced through the sample feed line 308 either batchwise or in a continuous fashion (pump III) 316. Eluate through each end of the column 318, 320 is monitored and fractionated with a fraction collector 322, 324.

FIG. 6C illustrates procedure for foam CCC. The separation is initiated by rotating the column 402 at the desired speed (usually at 500 rpm). Then, the liquid containing surfactant 304 is introduced through the tail end of the column 302 (pump I) 306 while the $N_2$ gas phase 308 is fed through the head end at 80 psi. The needle valve 310 on the flow line 312 from the head end is opened so that the desired amount of foam 314 is eluted through the tail outlet. After the steady state hydrodynamic equilibrium is reached, the sample solution is introduced through the sample feed line 316 either by a batch injection or in a continuous fashion (pump II) 318. The enriched foam 314 is collected through the tail with a foam collector 310 while the stripped liquid 312 is collected through the head with a fraction collector 322.

Figure 7:
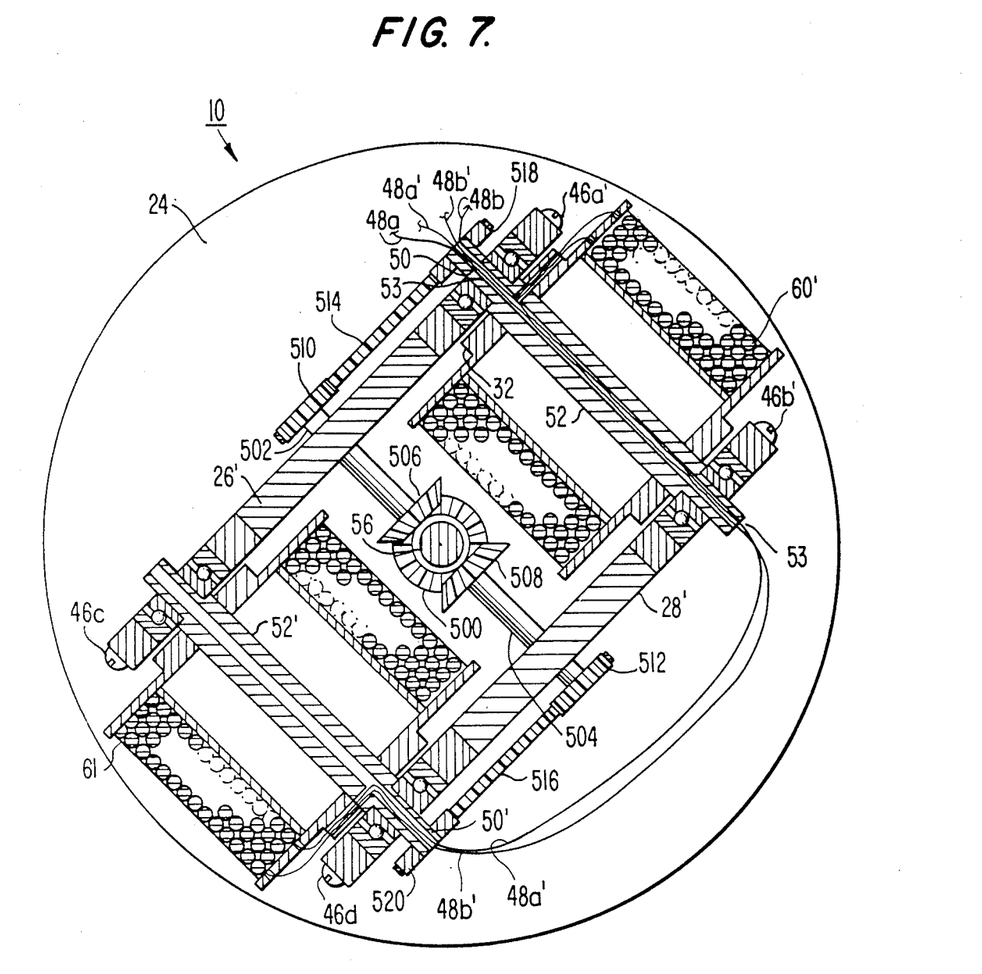
FIG. 7 shows a cross-sectional view of another preferred embodiment of an apparatus according to the present invention, the view being analogous to that of FIG. 4B.

FIG. 7 shows another embodiment 10' of the present invention, in the same view as the first embodiment is shown in FIG. 4B. In the embodiment of FIG. 7, a stationary miter gear 500 is rigidly mounted to the bottom plate of the centrifuge concentrically around central shaft 56. The rotation of central shaft 56, along with rotary plate 24, causes the rotation of shafts 502, 504 by the engagement of stationary miter gear 500 with identical planetary miter gears 506 and 508, respectively. Shafts 502, 504 are attached at their outer ends to toothed pulleys 510 and 512, respectively. Pulleys 510, 512 turn, respectively, toothed belts 514 and 516. Toothed belts 514, 516, respectively, engage and rotate gears 518 and 520, which in turn cause the respective rotation of attached column holders 52 and 52', along with columns 60 and 61. Parts 26', 28', 50', 52', 46a' and 46b' are analogous to parts 26, 28, 50, 52, 46a and 46b respectively.

By virtue of the embodiment of FIG. 7, the substitution of a second functional column 61 in place of counterweight 34 of the embodiment shown in FIGS. 4a and 4b is facilitated. Flow tubes 48a' and 48b' from the seocnd column holder 52' enter the first column holder 52 through the hole 53 to join flow tubes 48a and 48b at the other end of the hole where all four tubes, 48a, 48b, 48a' and 48b', are bundled together to reach the sidehole of the central shaft of the centrifuge as illustrated in FIGS. 4A–5A. If the two columns 61 and 60' are to be connected in series, flow tubes 48a' and 48b' should be connected to 48a and 48b repsectively near the exit of column holder hole 53. The column holder 52' and column 61 may also be replaced by a counterweight.

The design of the apparatus shown in FIG. 7 is superior to that in FIGS. 4A and B in terms of mechanical stability and dynamic balancing and therefore suitable to application of high revoluational speed.

What is claimed is:

1. An apparatus for countercurrent chromatography, comprising:
   a central shaft rotatable about its longitudinal axis;
   a first column holding means rotatable about a longitudinal axis of said first column holding means and holding a first chromatographic column, said first chromatographic column being wrapped around the longitudinal axis of said first column holding means, said first column holding means being mounted for revolution around the longitudinal axis of said central shaft with the longitudinal axis of the column holding means constantly positioned tangent to and coplanar with a path defined by the revolution of said first column holding means about said central shaft;

means for connecting said central shaft to said first column holding means so that the rotation of said central shaft causes the rotation and revolution of said first column holding means, and;

a frame means for revolving around the longitudinal axis of the central shaft, said frame means including upper and lower plates and two side plates extending between said upper and lower plates, said first column holding means being fixed to and between said side plates for revolving therewith.

2. The apparatus of claim 1, wherein said first column holding means is mounted for revolution and rotation at the same angular velocity.

3. The apparatus of claim 2, further comprising a motor for rotating said central shaft about its longitudinal axis.

4. The apparatus of claim 1, wherein said upper and lower plates are essentially parallel, said two side plates are essentially parallel and extend perpendicularly between said upper and lower plate, and said first column holding means is essentially perpendicular to said side plates.

5. The apparatus of claim 4, further comprising:
a stationary pulley concentrically fixed about an outer periphery of an end of said central shaft, said side plate being fixed around said central shaft for revolving therewith,
a countershaft extending through said upper and lower plates and essentially parallel to said side plates,
a toothed pulley concentrically fixed about an outer periphery of an end of said countershaft, corresponding to the end of said central shaft having said stationary pulley attached,
a first miter gear concentrically fixed to an outer periphery of a portion of said countershaft between said upper and lower plates for rotation with said countershaft,
a second miter gear concentrically fixed to an outer periphery of a column holder shaft of said column holder means for rotation therewith, engaged with and identical to said first miter gear, and
means for transmitting the rotation of said stationary pulley to said toothed pulley.

6. The apparatus of claim 5, wherein said rotation transmitting means is a toothed belt engaged with said stationary pulley and said toothed pulley.

7. The apparatus of claim 4, further comprising:
a stationary miter gear fixed on a stationary bottom plate of said apparatus and extending concentrically around said central shaft;
a first planetary miter gear engaged with said stationary miter gear;
a first gear shaft extending perpendicular to said central shaft, said first gear shaft being connected at one end to said first planetary miter gear for rotation therewith and at an opposite end extending through one of said side plates and being fixed to a first toothed pulley for rotation therewith;

a second toothed pulley fixed about an end of a first column holding shaft of said first column holding means corresponding to said end of said first gear shaft fixed to said first toothed pulley, for rotation therewith;
means for transmitting the rotation of said first toothed pulley to said second toothed pulley.

8. The apparatus of claim 7, wherein said first rotation transmitting means comprises a first toothed belt.

9. The apparatus of claim 7, further comprising:
a second planetary miter gear engaged with said stationary miter gear;
a second gear shaft extending perpendicular to said central shaft, said second gear shaft being connected at one end to said second planetary miter gear for rotation therewith and at an opposite end extending through the other of said side plates and being fixed to a third toothed pulley for rotation therewith;
a second column holding means rotatable about a longitudinal axis thereof for holding a second chromatographic column to be wrapped around the longitudinal axis of said second column holding means, said second column holding means being mounted for revolution about said longitudinal axis of said central shaft with said second column holding means constantly positioned tangent to a path defined by the revolution of said second column holding means, said second column holding means being fixed and essentially perpendicular to said side plates for revolving therewith, and being positioned symmetrically opposite said first column holding means with respect to said central shaft;
a fourth toothed pulley fixed about an end of a column holding shaft of said second column holding means corresponding to said end of said second gear shaft fixed to said third toothed pulley, for rotation therewith;
a second means for transmitting the rotation of said third toothed pulley to said fourth toothed pulley.

10. The apparatus of claim 9, wherein said second rotation transmitting means comprises a second toothed belt.

11. The apparatus of claim 9, wherein a second chromatographic column is wrapped about said second column holder.

12. A method of countercurrent chromatographic separation, comprising the steps of:
placing first and second immiscible fluid phases in a chromatographic column wrapped around a cylindrical column holder for rotation therewith, said chromatographic column having a head and a tail end and a central first longitudinal axis, said chromatographic column being fixed within a frame with respect to a second longitudinal axis positioned away from said column holder;
rotating said column holder about said central first longitudinal axis while simultaneously and synchronously revolving said column holder around said second longitudinal axis, positioned away from said column holder, in a manner such that the longitudinal axis of said column holder is constantly tangent to and coplanar with a path defined by the revolution of said column holder around said second longitudinal axis, whereby eluent is discharged at said tail or head end;
collecting said eluent discharged from said tail or head end.

13. The method of claim 12, wherein said first fluid phase is flowed through said column from said head end to said tail end and said second fluid phase is flowed through said column from said tail end to said head end.

14. The method of claim 12, wherein said first fluid phase is a stationary phase and said second phase is a mobile phase locally comprising a sample.

15. The method of claim 14, whereby said sample is caused to flow from one end of said column, through said stationary phase, to the other end of said column.

16. The method of claim 14, wherein said stationary phase comprises a foam at one end of said column and a liquid at the other, said mobile phase comprises a sample, said sample is injected into the middle of said column and eluent therefrom is collected at said head or tail end.

17. The method of claim 12, wherein a sample is injected into the middle of said column and eluent therefrom is collected at said head or tail end.

* * * * *